US005952215A

United States Patent [19]
Dwulet et al.

[11] Patent Number: 5,952,215
[45] Date of Patent: *Sep. 14, 1999

[54] ENZYME COMPOSITION FOR TISSUE DISSOCIATION

[75] Inventors: Francis E. Dwulet, Greenwood; Marilyn E. Smith, McCordsville, both of Ind.

[73] Assignee: Roche Diagnostics Corporation, Indianapolis, Ind.

[ * ] Notice: This patent is subject to a terminal disclaimer.

[21] Appl. No.: 09/184,616

[22] Filed: Nov. 2, 1998

Related U.S. Application Data

[63] Continuation of application No. 08/760,893, Dec. 6, 1996, Pat. No. 5,830,741.

[51] Int. Cl.$^6$ .............................. C12N 9/52; C12N 9/00
[52] U.S. Cl. ......................................... 435/220; 435/183
[58] Field of Search ..................................... 435/220, 183

[56] References Cited

U.S. PATENT DOCUMENTS

| | | | |
|---|---|---|---|
| 3,201,325 | 8/1965 | Barton et al. | 435/220 |
| 3,705,083 | 12/1972 | Chlulli et al. | 435/220 |
| 3,821,364 | 6/1974 | Chiulli et al. | 424/94.67 |
| 4,256,846 | 3/1981 | Nonaka et al. | 435/68.1 |
| 4,431,544 | 2/1984 | Atkinson et al. | 210/635 |
| 4,431,546 | 2/1984 | Hughes et al. | 210/656 |
| 4,732,758 | 3/1988 | Hurion et al. | 424/94.2 |
| 4,797,213 | 1/1989 | Parisius et al. | 210/651 |
| 4,868,121 | 9/1989 | Scharp et al. | 435/268 |
| 4,873,359 | 10/1989 | Chmurny et al. | 560/40 |
| 4,946,792 | 8/1990 | O'Leary | 435/268 |
| 5,079,160 | 1/1992 | Lacy et al. | 435/381 |
| 5,116,615 | 5/1992 | Gokcen et al. | 424/94.2 |
| 5,120,656 | 6/1992 | O'Leary et al. | 435/1.1 |
| 5,173,295 | 12/1992 | Wehling | 424/94.67 |
| 5,177,017 | 1/1993 | Lin et al. | 435/252.33 |
| 5,273,904 | 12/1993 | Langley | 435/283.1 |
| 5,322,790 | 6/1994 | Scharp et al. | 435/268 |
| 5,332,503 | 7/1994 | Lee et al. | 210/635 |
| 5,422,261 | 6/1995 | Lee et al. | 435/219 |
| 5,753,485 | 5/1998 | Dwulet et al. | 435/220 |
| 5,830,741 | 11/1998 | Dwulet et al. | 435/220 |

FOREIGN PATENT DOCUMENTS

| | | |
|---|---|---|
| 0 191 613 | 8/1986 | European Pat. Off. . |
| 91/14447 | 10/1991 | WIPO . |
| 96/00283 | 1/1996 | WIPO . |

OTHER PUBLICATIONS

Bond et al., Characterization of the Individual Collagenases from *Clostridium histolyticum*, 1984, *Biochemistry*, vol. 23, No. 13, pp.3085–3091.

Bond et al., "Purification and Separation of Individual Collagenases of *Clostridium histolyticum* Using Red Dye Ligand Chrometography", 1984, *Biochem*, vol. 23, No. 13, pp. 3077–3085.

Dean et al., "Protein Purification Using Immobilized Trizine Dyes", 1979, *Journal of Chromatography*, No. 165, pp. 301–319.

Emod et al., "Five Sepharose–Bound Ligands for the Chromatographic Purification of *Clostridium* Collagenase and Clostripain," 1977, *FEBS Letters*, vol. 77, No. 1, pp. 51–56.

Hatton et al., "The Role of Proteolytic Enzymes Derived From Crude Bacterial Collagenase in the Liberation of Hepatocytes From Rat Liver," 1983, *J. Biochem*, 137, pp. 311–318.

Hefley et al., "Enzymatic Isolation of Cells from Bone: Cytotoxio Enzymes of Bacterial Collagenase," 1981, *Am. J. Physiology*, 240, pp. C234–C238.

Hefley et al., "Enzymatic Isolation of Cells From Neonatal Calvaria using Two Purified Enzymes From *Clostridium histolyticum*," 1983, *Experimental Cell Research*, 149, pp. 227–236.

Hefley et al., "Utilization of FPLC–Purified Bacterial Collagenase From the Isolation of Cells from Bone," 1987, *Journal of Bone and Mineral Research*, vol. 2, No. 7, pp. 505–516.

Kobayashi et al, "Purification and Characterization of Myosin from Bovine Thyroid," Nov. 25, 1977, *The Journal of Biological Chemistry*, vol. 252, No. 22, pp. 8285–8291.

Kono, Purification and Partial Characterization of Collageholytic Enzymes From *Clostridium histolyticum*, Mar. 1968, *Biochemistry*, vol. 7, No. 3, pp. 1106–1114.

Kula et al., "Consecutive Use of ω–Aminoalkylagaroses. Res. and Purif. of Clostripain and Collagenase from *C. histolyticum*," 1976, *Biochem. & Bioph. Res. Comm.*, vol. 69, No. 2, pp. 389–396.

McShane et al., "Protease Activity In Pancreatic Islet Isolation by Enzymatic Digestion," 1989, *Diabetes*, vol. 38, Supp. 1, pp. 126–128.

Patel, "Biotechnology: Applications and Research," 1985, published by Technomic Publishing Company, Inc., Lancaster, Pennsylvania, pp. 534–562.

Sharefkin et al., "Adult Human Endothelial Cell Enzymatic Harvesting," 1986, *Journal of Vascular Surgery*, vol. 4, No. 6, pp. 567–577.

Silink et al., "γ–Glutamyl Hydrolase (Conjugase)," Aug. 10, 1975, *The Journal of Biological Chemistry*, vol. 250, No. 15, pp. 5982–5994.

Stevens et al., "Dissociation of Lung Tissue into Monodispersed Cells by Use of Purified Collagenase," 1979, *J. Appl. Biochem.*, pp. 460–470.

Van Wart et al., "Complementary Substrate Specificities of Class I and Class II Collagenase From *Clostridium histolyticum*," 1985, *Biochemistry*, vol 24. No. 23, pp. 6520–6526.

(List continued on next page.)

*Primary Examiner*—John P. Weber
*Attorney, Agent, or Firm*—Barnes & Thornburg

[57] ABSTRACT

An enzyme composition and its use for isolating cells or cell clusters from tissue is disclosed. The composition includes two purified collagenase enzymes and an endoprotease. The ratio of the total FITC casein activity of the enzyme composition to the Wunsch units of activity of the masses of collagenase I and collagenase II is about 85:1 to about 3,900:1.

11 Claims, No Drawings

OTHER PUBLICATIONS

Wolters et al., "An Analysis of the Role of Collagenase and Protease in the Enzymatic Dissociation of Rat Pancreas for Islet Isolation," 1992, *Diabetologia*, 35, pp. 735–742.

Wolters, et al., "Different Roles of Class I and Class II *Clostridium Histolyticum* Collagenase In Rat Pancreatic Islet Isolation,", 1995, *Diabetes*, vol. 44, pp. 227–233.

Worthington, "Worthington Enzyme Manual—Enzymes and Related Biochemicals," 1988, Worthington Biochemical Corporation, pp. 93–101.

Jauregui et al., "Primary Cultures of Rat Hepatocytes in Hollow Fiber Chambers," 1994, *In Vitro Cell Dev. Biol.*, vol. 30A, pp. 23–29.

Tavakol et al., "Enhanced Dissolution of Nucleus Pulposus: Combined Enzyme Approach,", 1984, *Surgical Forum*, 37, pp. 491–494.

Maruyama et al., "Preparation of Single Smooth Muscle Cells from Guinea Pig Taenia Coli by Combination of Purified Collagenase and Papain,", 1987, *J. Pharmacol. Meth.*. 18, pp. 151–161.

Maruyama et al., "Improvement of a Procedure for Preparing Single Smooth Muscle Cells from Guinea Pig Taenia Coli by Purified Collagenase and Papaln,", 1988, *J. Pharmacol. Meth.*, 19, pp. 155–164.

Suggs, et al., "Enzymatic Harvesting of Adult Human Saphenous Vein Endothelial Cells: Use of Chemically Defined Combination of Two Purified Enzymes to Attainable Cell Yields Equal to Those Attained by Crude Bacterial Collagenase Preparations," *J. Vasc. Surg.,*, 19(1), pp. 205–213.

Gill et al., Transplantation Proceedings, vol. 27(6), "Safety Testing of Liberase, A Purified Blend for Human Islet Isolation", pp. 3276–3277, Dec. 1995.

Linetsky et al., Transplantation Proceedings, vol. 27(6), "Comparison of Collagenase Type P and Liberase During Human Islet Isolation Using the Automated Method", p. 3264, Dec. 1995.

1

ENZYME COMPOSITION FOR TISSUE DISSOCIATION

This application is a continuation of application Ser. No. 08/760,893, filed on Dec. 06, 1996, now U.S. Pat. 5,830,741.

FIELD OF THE INVENTION

This invention relates to compositions for the enzymatic dissociation of extracellular tissue matrices to allow tissue remodeling and the efficient isolation of viable cells and cell clusters from tissue.

BACKGROUND OF THE INVENTION

The enzymatic dissociation of tissue into individual cells and cell clusters is useful in a wide variety of laboratory, diagnostic and therapeutic applications. These applications involve the isolation of many types of cells for various uses, including microvascular endothelial cells for small diameter synthetic vascular graft seeding, hepatocytes for gene therapy, drug toxicology screening and extracorporeal liver assist devices, chondrocytes for cartilage regeneration, and islets of Langerhans for the treatment of insulin-dependent diabetes mellitus. Enzyme treatment works to fragment extracellular matrix proteins and proteins which maintain cell-to-cell contact. Since collagen is the principle protein component of tissue ultrastructure, the enzyme collagenase has been frequently used to accomplish the desired tissue disintegration.

Different forms of crude bacterial collagenase derived from *Clostridium histolyticum* are commercially available and are used to dissociate cells and cell clusters from tissue. These crude collagenases, derived from cell culture supernatants, typically contain a mixture of protease enzymes (exhibiting both collagenolytic and non-specific proteolytic activities) and non-protease components (e.g., fermentation by-products, media components, pigments, other enzymes such as phospholipase, and endotoxins).

Analysis of commercially-available crude collagenases has shown extreme variations in the concentration and ratios of the protease and non-protease components. Such compositional variability is reflected as well in the variability and consequent lot-to-lot unpredictability of collagenase product performance in tissue dissociation protocols. In addition to this inherent activity variability, each lot of commercial collagenase loses activity and performance characteristics over time. Finally, in addition to these problems associated with compositional variability, the use of crude collagenases in cell harvest/tissue dissociation protocols usually results in less- than-desired results in terms of recovery of cell viability, cell number and cell function. These problems are particularly significant where the cells are targeted for use in transplantation or for monitoring the impact of effector molecules on cell function. For example, it has been demonstrated that the efficacy of islet transplantation is dependent in part on the mass of islets and their viability. In addition, the drug detoxification function of recovered hepatocytes is significantly impaired by damage to the cells occurring during liver tissue dissociation and cell isolation. For most uses of recovered cells it is critical for optimum cell performance that damage to the recovered cells and cell clusters be minimized.

Skilled practitioners have recognized the importance of the consistent/predictable activity of protease enzymes used in tissue dissociation protocols for efficacious cellular isolation (i.e., maintaining cellular integrity, recovering larger cell clusters and more cells or cell clusters). Specifically, the purity of collagenase compositions and the desirability of the presence of defined amounts of both *C. histolyticum* collagenase class I (collagenase I) and collagenase class II (collagenase II) enzymes with at least two neutral proteases has been found to influence the efficacy of pancreatic islet isolation. However, there still exists a need for identifying optimized enzyme compositions which provide for rapid dissociation of tissue and recovery of a greater number of viable cells.

SUMMARY OF THE INVENTION

The present invention provides an enzyme composition prepared by combining defined masses of purified proteases, including collagenase I and collagenase II from *C. histolyticum* and an amount of an endoprotease such that the ratio of the total FITC casein units of activity of the enzyme composition to the Wunsch units of activity of the masses of collagenase I and collagenase II is about 85:1 to about 3,900:1. When used in tissue dissociation protocols for cell isolation the resulting enzyme composition functions to effect improved, more rapid dissociation of extracellular matrices and it allows recovery of higher yields of the desired cells with improved viability relative to the number and viability of cells harvested using enzyme compositions of the prior art, including crude collagenase compositions.

In another embodiment of this invention there is provided an enzyme composition consisting essentially of collagenase I and collagenase II from *C histolyticum* and an endoprotease, wherein the ratio of the mass of collagenase II to the mass of collagenase I plus the mass of collagenase II in the enzyme composition is about 0.3 to about 0.6. The resulting enzyme composition is also an improvement over previously known compositions because of its ability to more rapidly dissociate extracellular tissue matrices and allow recovery of a larger number of viable cells.

This invention also provides a method of preparing an enzyme composition adapted for isolating living cells from tissue which includes the step of combining known masses of collagenase I and collagenase II from *C. histolyticum* and an amount of an endoprotease sufficient to raise the total FITC casein activity of the enzyme composition to a level such that the ratio of the total FITC casein activity of the enzyme composition to the total Wunsch unit activity of the masses of collagenase I and collagenase II in the enzyme composition is about 85:1 to about 3,900:1.

DETAILED DESCRIPTION OF THE INVENTION

This invention is based on the discovery that collagenase I and collagenase II from *C. histolyticum* may be combined with defined amounts of an endoprotease to provide a novel enzyme composition having activity profiles optimal for isolating cells from donor organ tissue. More specifically, it has been discovered that optimal enzymatic degradation of extracellular tissue matrices and concomitant efficient liberation of viable cells and cell clusters from organ tissue can be achieved by using a collagenase enzyme composition prepared by adjusting the components of the composition so that the ratio of the total FITC casein activity of the enzyme composition to the Wunsch units of activity of the masses of collagenase I and collagenase II in the composition is about 85:1 to about 3,900:1 and is preferably about 130:1 to about 1,400:1. In one embodiment of the invention, there is provided an enzyme composition useful for efficient dissociation of rat liver tissue to provide a high yield of hepatocytes. That enzyme composition includes amounts of collagenase I and collagenase II from *C. histolyticum* and an endoprotease such that the ratio of the total FITC casein activity of the enzyme composition to the Wunsch units of activity of the masses of collagenase I and collagenase II in the composition is about 250:1 to about 600:1, with an average ratio of about 400:1.

Another aspect of the present invention is optimizing mass ratios of the two component collagenase enzymes in enzyme compositions of this invention consisting essentially of collagenase I, collagenase II and an endoprotease. The optimal mass ratio of collagenase II to the total collagenase in the composition, collagenase II/(collagenase I +collagenase II), is about 0.3 to about 0.6. When collagenase I and collagenase II from *C. histolyticum* are combined in this mass ratio with an endoprotease, the resulting enzyme composition is particularly useful to recover cells and cell clusters from tissue samples in greater number, with higher viability, and with improved reproducibility over tissue dissociation protocols using previously known collagenase enzyme compositions. In one enzyme composition embodiment of this invention useful for dissociating rat liver, the mass ratio of collagenase II to the total collagenase in the composition is about 0.35 to about 0.45.

The enzyme compositions of the present invention include both collagenase I and collagenase II from *C. histolyticum*. Collagenase I and collagenase II are purified from *C. histolyticum* crude collagenase by a variety of methods known to those skilled in the art, including dye ligand affinity chromatography, heparin affinity chromatography, ammonium sulfate precipitation, hydroxylapatite chromatography, size exclusion chromatography, ion exchange chromatography, and metal chelation chromatography. Crude collagenase is commercially available from many sources (e.g., Collagenase P from Boehringer Mannheim Corporation).

The endoprotease component of the present enzyme composition can be any endoprotease, including a serine protease (e.g., trypsin, chymotrypsin, elastase), a cysteine protease (e.g., papain, chymopapain) and is preferably a neutral protease (e.g., *C. histolyticum* neutral protease, dispase, or thermolysin (all EC 3.4.24.4). (EC stands for Enzyme Commission classification. EC 3.4.24.4 is the classification for microbial metalloproteinases.)

For dissociation of a 6 to 12 gram rat liver to recover hepatocytes, the activity of the masses of collagenase I and collagenase II in the enzyme composition is about 7.7 to about 62.7 Wunsch units, preferably about 15.1 to about 52.6 Wunsch units, and more preferably about 24 to about 33 Wunsch units with an average activity of about 30 Wunsch units. The total FITC casein activity of this enzyme composition is about 5,500 to about 29,700 FITC casein units, preferably about 7,000 to about 22,000 FITC casein units, and more preferably about 8,500 to about 14,500 FITC casein units with an average activity of about 12,000 FITC casein units. Accordingly, the ratio range of FITC casein units of the composition to Wunsch units of the composition is 5,500/62.7 to 29,700/7.7 or about 85:1 to about 3,900:1, preferably 7,000/52.6 to 22,000/15.1 or about 130:1 to about 1,400:1, and more preferably 8,500/33 to 14,500/24 or about 250:1 to about 600:1 with an average activity ratio of 12,000/30 or about 400:1.

In addition to the dissociation of liver for isolation of hepatocytes, the above composition is useful for the dissociation of epidermal fat for the isolation of microvascular endothelial cells. The above composition is also expected to be useful for dissociating pancreas tissue, topical treatment for burn and ulcer clearing and for wound healing, treatment of Peyronie's disease and reformation of abnormal or herniated discs. In general, the composition of the present invention is useful for any application where the removal of cells or modification of an extracellular matrix are desired.

For some applications, it may be preferred that the enzyme composition be substantially free of endotoxins. It may also be desirable for the enzyme composition to be substantially free of the enzyme clostripain, although generally clostripain does not seem to affect performance of the enzyme composition. These undesirable components, which are both present in crude collagenase obtained from *C. histolyticum*, can be separated from the purified collagenase I and II components using one or more of the purification methods described above. "Substantially free" as used herein to describe this invention means that effort is or has been made to exclude referenced impurity from the composition and that such impurity, if present at all in the composition, is present in but trace amounts, typically less than 2% by weight, more typically less than 1% by weight and in any event less than an amount which would affect the aggregate functionality of the composition.

Enzyme compositions of this invention may be prepared by mixing either a specific number of activity units (i.e., Wunsch units of collagenase I and collagenase II) or specific masses of the preferably purified enzymes. Following are enzyme assays for collagenase, neutral protease and clostripain that were used to define the specific activities of the purified collagenase components as well as the total activity (FITC) of the entire enzyme composition. Those skilled in the art will recognize that enzyme assays other than those disclosed below may also be used to define and prepare functionally equivalent enzyme compositions.

Collagenase activity assay

Collagenase activity was measured using a synthetic peptide substrate according to the method of Wunsch & Heidrich (*Z. Physiol Chem.* 1963; 333:149). This is a standard method well known to those skilled in the art of collagenase purification. The measured activity of collagenase I using the Wunsch peptide as a substrate typically ranged from 0.2 to 0.6 units (U)/milligram (mg) and was more typically 0.3 to 0.5 U/mg. The measured activity of collagenase II using the Wunsch peptide as a substrate typically ranged from 9.5 to 13.5 U/mg and was more typically 11 to 13 U/mg. One Wunsch unit (U) of activity is defined by the hydrolysis of 1 micromole ($\mu$mol) peptide per minute at 25°C., pH 7.1. A description of the test procedure used for the collagenase activity assay is given below. Sample Dilution Buffer (100 millimoles (mM)/liter (l) tris-(hydroxymethyl)-aminomethane (Tris). pH 7.1): 1.21 gram (g) Tris was dissolved in deionized (DI) water. The pH was adjusted to 7.1 with 1.0 Normal (N) hydrochloric acid (HCl) and the volume was adjusted to 100 milliliters (ml) with DI water.

PZ-Pro-Leu-Gly-Pro-D-Arg substrate: Each blank or test sample was assayed in duplicate. Total amount of substrate needed for assay =2 mg of substrate for each test performed, plus 2 mg of substrate extra. (For example, 2 samples tested in duplicate +duplicate blank tubes =6 assay tubes. The target amount of substrate needed is 14.0 mg.) The total amount of substrate weighed out was divided by 50 to determine the number of milliliters of methanol needed to dissolve the substrate. The calculated amount of methanol was added to the substrate. The substrate was mixed thoroughly by vortexing until totally dissolved. Sample Dilution Buffer was added to the dissolved substrate to a final volume so that the concentration of substrate was 1 mg/ml.

100 mM/l Calcium Chloride (CaCl$_2$): 1.47g CaCl$_2$, Formula Weight (FW) 147, was dissolved in DI water. The volume was adjusted to 100 ml with DI water.

25 mM/l Citric Acid: 0.525g Citric acid, FW 210..1, was dissolved in DI water. The volume was adjusted to 100 ml with DI water.

Assay Mixture. 2.0 ml of PZ-Pro-Leu-Gly-Pro-D-Arg Substrate and 0.4 ml 100 mM

CaCl$_2$ were added to 12×75 millimeter (mm) test tubes and capped. The assay mixtures were allowed to equilibrate in a water bath to 25° C. before beginning the assay. One tube was prepared for each duplicate blank or sample tested.

Extraction Mixture: 5.0 ml of ethyl acetate and 1.0 ml of 25 mM/l citric acid were added to 16×125 mm test tubes. Each tube was capped. One tube was prepared for each duplicate blank or sample tested.

Drying tubes: 0.35 to 0.4 g anhydrous sodium sulfate was added to 16×125 mm test tubes. Each tube was capped. One tube was prepared for each duplicate blank or sample tested.

Assay Procedure: All concentrated and diluted enzyme samples were kept at 2° C. to 8° C. until added to the substrate. A sample of either the entire enzyme composition or one of its components (e.g., collagenase I, collagenase II, or neutral protease) was diluted with Sample Dilution Buffer to a concentration range of 0.05 to 0.8 mg/ml, depending upon estimated sample activity. The assay incubation time was started after 100 microliters ($\mu$l) of blank control (Sample Dilution Buffer was used as a blank) was added to the first tube of Assay Mixture. The Assay Mixture was then capped, mixed thoroughly, and placed in a 25° C. water bath. At 60 second intervals, 100 $\mu$l of the next blank or test sample was added to a tube of Assay Mixture in the same manner. Each Assay Mixture was incubated at 25° C. for 15 minutes (min) from the time the blank or test sample was added. After 15 min of incubation, 0.5 ml of the first blank Assay Mixture was transferred to a tube containing Extraction Mixture. The Extraction Mixture tube was capped and mixed thoroughly by vortexing for 20 seconds. At 60 second intervals, the remaining blank or test samples were transferred to Extraction Mixture tubes and mixed in the same manner, so that total incubation time for each sample was 15 min. 3 ml of the organic phase (top) from each Extraction Mixture was pipetted into a Drying Tube. The Drying Tubes were capped, mixed and incubated at room temperature in a fume hood for 30 to 60 min. The tubes were mixed again during this period. The organic phase was pipetted into quartz cuvettes and, using a temperature-controlled spectrophotometer at 25° C., the absorbance was read at 320 nanometers (nm) for each blank and sample.

Calculations: $A_{320}$=Average absorbance of sample —Average absorbance of buffer blank. Activity (U/ml)= ($A_{320}$×2.5×5×Dilution Factor)/(21×0.10×0.5×15). Simplified, U/ml=$A_{320}$×0.79×Dilution Factor. The U/mg specific activity was calculated for each sample by the following calculation: specific activity (U/mg)=(U/ml)/(mg/ml).

Neutral Protease Activity Assay

Neutral protease activity was measured by the liberation of trichloroacetic acid (TCA) soluble fluorescent peptides from the substrate FITC-casein according to a modified version of the method of Twining (*Anal. Biochem.*1984; 143:30). Fluorescent peptides were quantified using an excitation wavelength of 491 nm and an emission wavelength of 525 nm. The range of measured FITC-casein specific activity for the neutral protease dispase was typically 600 to 1400 U/mg and was more typically 1100 to 1400 U/mg. The range of measured FITC-casein specific activity for the neutral protease thermolysin was typically 3000 to 6500 U/mg and was more typically 3500 to 6000 U/mg. One unit of activity generates 100,000 fluorescence units (counts per second) corrected for background per minute at 37° C., pH 7.5. A description of the test procedure used for the neutral protease activity assay is given below.

Sample Dilution Buffer (100 mM/l Tris. 10 mM/l CaCl$_2$, pH 7.5): 6.06g Tris and 0.74 g CaCl$_2$ were dissolved in DI water. The pH was adjusted to 7.5 with 1.0N HCl and the volume adjusted to 500 ml with DI water.

FITC-Casein Substrate Solution (0.25% w/v): 50.0 mg FITC-casein was dissolved in the Sample Dilution Buffer. The volume was adjusted to 20.0 ml with Sample Dilution Buffer. Quenching Solution (5.0% w/v): 5.0 g of Trichloroacetic Acid was dissolved in DI water. The volume was adjusted to 100 ml with DI water. Neutralization Solution (500 mM/l Tris: pH 8.5): 30.3 g Tris was dissolved in DI water. The pH was adjusted to 8.5 with 1.0N HCl and the volume was adjusted to 500ml with DI water.

Assay Procedure: All concentrated and diluted enzyme samples were kept at 2° C. to 8° C. until added to the substrate. Each blank or test sample was assayed in duplicate. A sample of either the entire enzyme composition or one of its components (e.g., collagenase I, collagenase II, or neutral protease) was diluted with Sample Dilution Buffer to a concentration range of 1 to 50 micrograms ($\mu$g)/ml, depending upon estimated sample activity. 10 $\mu$l of the diluted samples were added to 40 $\mu$l of FITC-casein Substrate Solution in 1.5 ml Eppendorf tubes (the Sample Dilution Buffer was used as a blank control) and incubated for 45 min with shaking at 37° C. in a water bath. The tubes were removed from the water bath and 120 $\mu$l of the Quenching Solution was added. The tubes were vortexed and left at room temperature for at least 60 min. The tubes were then centrifuged in a microcentrifuge at 14,000 rpm for 2 min. 50 $\mu$l of the supernatant was removed and added to 2ml of Neutralization Buffer in a cuvette. The cuvette was capped and inverted to mix the solution. Fluorescence was then measured (excitation wavelength 491 nm, emission wavelength 525 nm, slit width 0.2 nm).

Calculations: CPS =Average enzyme sample fluorescence —Average buffer blank fluorescence. Activity (U/ml)= (CPS×0.17 ml ×Dilution factor)/(0.05 ml×0.01 ml ×45 min. ×100,000). Simplified, U/ml =CPS ×0.0000755 ×Dilution factor. The linear range for the SPEX fluorimeter is from 4000 to 100,000 CPS.

The substrate casein used in the assay for neutral proteases described above can also act as a general substrate for a wide variety of protease activities including trypsin, clostripain, dispase, thermolysin, and many others. The preferred ranges for FITC casein activity of the total enzyme composition described herein were measured and defined as units of activity of the final enzyme composition and were not the actual units of the neutral protease components measured alone prior to mixing.

Clostripain Activity Assay

Clostripain activity was measured by the esterolysis of N-benzoyl-L-arginine ethyl ester (BAEE) according to a modification of the method of Whitaker and Bender (*J. Am. Chem. Soc.* 1965; 87:2728). Clostripain is a cysteine protease activated by reducing agents such as dithiothreitol (DTT). Measured clostripain activity is the difference between DTT-activated enzyme and non-DTT-treated enzyme. The activities described were generated using 1.8 mM BAEE. One unit is defined as the hydrolysis of 1 µmol BAEE per min at 25° C., pH 7.6. A description of the test procedure used for the clostripain activity assay is given below.

Phosphate Buffer (75 mM/l): 1.17 g sodium phosphate, monobasic ($NaH_2PO_4$) was dissolved in DI water. The volume was adjusted to 100 ml with DI water and labeled "solution A".1.07 g sodium phosphate, dibasic ($Na_2HPO_4$) was dissolved in DI water. The volume was adjusted to 100 ml with DI water and labeled "solution B". The pH value of solution B was adjusted to 7.6 with solution A.

DTT Solution (7.5 mM/l): 28.9 mg dithiothreitol (DTT) was dissolved in DI water and the volume was adjusted to 25 ml with DI water.

BAEE Solution (1.8 mM/l): 15.4 mg BAEE was dissolved in DI water and the volume was adjusted to 25 ml with DI water.

10×Activating Solution (10 mM/l calcium acetate. 25 mM/l DTT): 17.6 mg calcium acetate and 38.6 mg DTT was dissolved in DI water and the volume was adjusted to 10.0 ml with DI water.

10×Blank Solution (10 mM/l calcium acetate): 17.6 mg calcium acetate was dissolved in RO/DI water and the volume was adjusted to 10.0 ml with DI water.

Sample Preparation: All concentrated and diluted enzyme samples were kept at 2° C. to 8° C. until added to the substrate. Collagenase I was diluted with a combination of 10×Activation Solution and DI water so that the final sample concentration was 0.15 mg/ml in 1×Activation Solution. (For example, to dilute a 26.7 mg/ml collagenase I sample to 0.15 mg/ml for assay, mix 10 µl of the 26.7 mg/ml collagenase I sample with 178 µl of 10×Activating Solution plus 1592 µl DI water.) Collagenase ll was diluted with a combination of 10×Activation Solution and DI water so that the final sample concentration was 0.4 mg/ml in 1×Activation Solution. (For example, to dilute a 31.2 mg/ml collagenase II sample to 0.4 mg/ml for assay, mix 10 µl of the 31.2 mg/ml collagenase II sample with 78 µl of 10×Activating Solution plus 692 µl DI water.) The samples were then incubated for 4.5 hours at room temperature.

Trypsin Blank Preparation: Trypsin blanks were prepared by repeating the sample dilutions using 10×Blank Solution in place of 10×Activating Solution and 1×Blank Solution in place of 1×Activating Solution.

Spectrophotometric Assay (wavelength 253 nm, final volume 0.93 ml. temperature 25°C.): A trypsin blank mixture and an activated sample mixture were prepared by mixing the following:

|  | Trypsin blank mixture | Activated sample mixture |
| --- | --- | --- |
| BAEE Substrate | 5.0 ml | 5.0 ml |
| 75 mM/l phosphate buffer pH 7.6 | 5.0 ml | 5.0 ml |
| DI water | 5.0 ml | — |
| 7.5 mM/l DTT Solution | — | 5.0 ml |

Four quartz cuvettes were placed in the spectrophotometer. 0.9 ml of the trypsin blank mixture was pipetted into each of the first two cuvettes. 0.9 ml of the activated sample mixture was pipetted into each of the remaining two cuvettes. The absorbance was read for 1.5 min to establish a blank rate (the blank rate should not exceed 0.01 delta ($\Delta$) $A_{253}$/min). The reaction was then started by pipetting 0.03 ml of the diluted Trypsin Blank Preparation into the two trypsin blank cuvettes and 0.03 ml of the diluted Sample Preparation into the two activated sample cuvettes and mixing thoroughly. Each cuvette was read for 1.5 min to determine the reaction rate. (The $\Delta A_{253}$/min should be between 0.007 and 0.040.)

Calculation: For each sample, the U/ml activity was calculated as follows: U/ml=[($\Delta A$/minute)×(dilution factor)×(0.93)×(1000)]/[(1150)×(0.03)]where $\Delta A$/minute =$\Delta A_{253}$/min sample −$\Delta A_{253}$/min blank. Simplified, U/ml =($\Delta A$/minute)×(dilution factor)×(26.96). The U/mg specific activity was calculated for each sample by the following calculation: specific activity (U/mg)=(U/ml)/(mg/ml).

EXAMPLE 1:

PURIFICATION OF COLLAGENASE I AND COLLAGENASE II FROM CRUDE BACTERIAL COLLAGENASE

Commercially available crude bacterial collagenase (Collagenase P, Boehringer Mannheim Corporation) was used as the starting material. Three dye ligand affinity chromatography supports from Amicon were found to perform acceptably. These supports were MATREX (registered trademark, W.R. Grace & Co.) Gel Blue A, MATREX Gel Red A, and MATREX Gel Green A. Comparable products from other suppliers were found to perform in a similar manner. For maximum recovery of activity, all purification steps were performed at 2° C. to 8°C.

The crude bacterial collagenase and the chosen support were equilibrated against a low ionic strength calcium-containing buffer at a pH between 6.0 to 7.5. For the best combination of purification efficiency, enzyme stability and resin capacity a pH range of 6.5 to 7.0 is preferable. For these chromatographies either 20 mM 4-[2- hydroxyethyl]-1- piperazine ethanesulfonic acid (HEPES) or 20 mM [bis-(2-hydroxyethyl)-imino]-tris-(hydroxymethyl)-methane (BIS-Tris), 1 mM calcium chloride pH 7.0 buffers were used for resin and enzyme equilibration. The crude bacterial collagenase was dissolved by suspending the lyophilized starting material in the selected equilibration buffer at a sample concentration of about 40 mg/ml. Concentrations of 1 to 100 mg/ml have been used with concentrations around 40 mg/ml having the best combination of enzyme stability and short sample loading times. Insoluble material can be removed by centrifugation and/or filtration through cellulose, cellulose acetate, polyethersulfone or other low protein binding membranes.

The clarified sample was applied to the resin at flow rates ranging from 0.1 to 2.0 centimeters (cm)/min. The purification is insensitive to flow rate so that flow rate which best fits the production schedule is used. Depending on the lot of resin, 10 to 15 mg of enzyme can be bound to the Red A and Green A resins which translates to a binding capacity of 20 to 40 mg of collagenase P per milliliter of these supports. The Blue A resin has about ½ of this capacity. After the sample has been loaded onto the column the unretained material is washed from the column by the application of equilibration buffer. Usually two to three column volumes of buffer is sufficient for this task.

The bound enzymes were recovered by elution from the resin using a salt and/or pH gradient. Elution buffers comprising 20 mM HEPES, 1 mM calcium chloride and 400 mM sodium chloride pH 7.5 or 20 mM Tris, 1 mM calcium chloride and 150 mM sodium chloride pH 9.0 were sufficient to recover the bulk of the bound proteolytic activity.

The dye ligand affinity purified collagenase enzyme mixture was further purified by strong cation exchange chromatography on SP Sepharose Fast Flow resin (registered trademark, Pharmacia, Inc.). Before use the resin was converted from the sodium form to the calcium form. This was accomplished by washing the resin with excess calcium chloride solution. A ½ column volume of 500 mM calcium chloride solution was sufficient to convert the packed resin into the calcium form. The packed calcium form resin and the dye ligand affinity purified enzyme solution were equilibrated against a low ionic strength calcium containing buffer maintained at a pH of between 6.5 and 7.5. For these chromatographies 20 mM HEPES, 5 mM calcium chloride pH 7.0 buffer was used for equilibration. The equilibrated dye ligand affinity purified enzyme mixture was applied to the calcium form SP Sepharose FF column at flow rates up to 8 cm/min. For most purifications a flow rate of 2 cm/min is most convenient for speed and ease of process control. After the sample was applied the collagenase enzymes were eluted by the application of equilibration buffer. Usually about two column volumes of buffer were sufficient to elute all of the collagenase enzymes from the column. Once the collagenase enzymes were eluted from the column the bound proteins (predominantly clostripain along with several non-protease proteins) can be eluted using a 5 to 100 mM calcium chloride gradient. This was accomplished using a 10 to 15 column volume linear gradient to recover the purified clostripain or by a step gradient to clean the column for reuse. On average one to two milligrams of clostripain were bound per milliliter of resin. It is important to saturate this resin with calcium because if this is not done the resin will remove calcium from the enzymes in the preparation which will result in increased degradation of the enzymes and poorer recoveries. It is expected that other strong cation exchange resins should perform in a similar manner as this resin.

The flow through fraction from the calcium saturated SP Sepharose FF column, which contained the collagenase enzymes and the clostridial neutral protease, was purified by anion exchange chromatography on either diethyl aminoethyl (DEAE) or trimethyl aminoethyl (Q) Sepharose Fast Flow (Pharmacia). Both the support and the enzyme sample were equilibrated against a low ionic strength calcium containing buffer with a pH of between 6.5 to 9.0. Within this pH range both resins yielded similar purification efficiencies and recoveries. However, because of its simpler regeneration and equilibration protocols, the Q Sepharose FF support was used. For these chromatographies 5 mM HEPES, 1 mNM calcium chloride pH 7.5 buffer was used. The equilibrated collagenase enzyme pool was applied to the equilibrated resin at flow rates up to 8 cm/min (usually at 1 to 2 cm/min). On average 20 to 50 mg of enzyme mixture were applied per ml of resin. Once the mixture was applied to the resin the enzymes were eluted by a 1 to 100 mM calcium chloride linear gradient. A 20 to 30 column volume gradient was used. The collagenase II enzyme eluted at about 15 to 20 mM calcium, the collagenase I eluted at about 30 to 35 mM calcium, and the neutral protease at about 60 to 70 mM calcium.

The recovered enzymes were equilibrated against 5 mM HEPES, 1 mM calcium chloride pH 7.5 buffer and stored frozen at or below −20°C. When purified in this manner and kept under these conditions the collagenase enzymes can be kept for at least two years without evidence of activity loss.

Collagenase I and II prepared in this manner have been found to be substantially free of clostripain. In our experience material prepared in this way has less than 3 BAEE units of clostripain activity and usually have one or less units of activity. This translates to a very high level of purity (98 to 99%) for both coliagenase components. Table 1 below shows the typical enzyme activities of the purified enzyme components.

TABLE 1

Typical enzyme activities of purified enzyme components

| Enzyme | Wunsch Activity | BAEE Activity | FITC casein Activity |
|---|---|---|---|
| collagenase I | 0.2–0.6 U/mg | | |
| collagenase II | 9.5–13.5 U/mg | | |
| clostripain | | 70–140 U/mg | |
| thermolysin | | | 3000–6500 U/mg |
| dispase | | | 600–1400 U/mg |

EXAMPLE 2:

PREPARATION OF AN ENZYME COMPOSITION FOR THE ISOLATION OF HEPATOCYTES FROM LIVER

Collagenase I and II, which have very high solubilities, were prepared and stored as frozen liquids as described above in Example 1. However, thermolysin has a much lower solubility and is much harder to get into solution, especially in concentrations greater than 2.0 mg/ml. To accomplish a reproducible solubilization of this enzyme a modification of the procedure presented by Matsubra (Methods in Enzymology v. 19 pp.642–651) was used. The desired mass of dry thermolysin (Boehringer Mannheim Corporation, Biochemicals cat. #161586) was placed in an appropriately sized container. Sufficient high purity water was added to prepare an 8 mg/ml thermolysin suspension. After mixing in an ice bath to hydrate the thermolysin crystals, sufficient cold dilute sodium hydroxide solution was added to adjust the pH to about 10.5 If necessary, the pH can be increased to 11.5 to insure complete solubilization. When solubilization was complete the solution had a light yellow to light tan color. The pH of this solution was then lowered to 8.5 using a dilute acetic acid solution. HEPES free acid also works well and is compatible with the buffer solution. After this solubilization process a thermolysin solution with a protein concentration of 5 to 6 mg/ml can be maintained for at least several hours at 0 to 8°C.

Enzyme compositions were prepared by mixing specific masses of each enzyme. The mass of each enzyme was determined based upon its absorbance at 280 nanometers. For collagenase I and II, a 1.0 mg/ml solution will have an absorbance of 1.4 absorbance units (AU) and a 1.0 mg/ml thermolysin solution will have an absorbance of 1.1 AU. Using these values, solutions of each component were prepared and the calculated number of absorbance units for each component were blended to prepare the desired mixtures.

The collagenase I and II samples from Example 1 above were thawed. (All operations should be performed at 0 to 8° C. to maximize enzyme stability.) A sample of collagenase I enzyme was prepared that contained 3.48 mg of protein (4.87 AU). To this sample was added a sample of collagenase II enzyme that contained 2.32 mg of protein (3.25 AU).

To this mixture of collagenase I and II, a volume of thermolysin solution was added that provided 1.82 mg of this enzyme (2.00 AU) and mixed well.

Once blended the enzyme composition can be kept in an ice bath for several hours without loss of activity. However, it is recommended for longer term storage that the composition be kept at −20° C. or lower as a frozen liquid or as a lyophilizate. Prepared in this way these blends are stable for several years. For a 6 to 12 gram liver the masses of enzymes shown in Table 2 below provided an optimal mixture for hepatocyte isolation.

TABLE 2

Enzyme Composition For Rat Liver Dissociation

| Enzyme | Weight | Absorbance units/milligram | Total absorbance units |
|---|---|---|---|
| collagenase I | 3.48 mg | 1.4 AU/mg | 4.87 AU |
| collagenase II | 2.32 mg | 1.4 AU/mg | 3.25 AU |
| thermolysin | 1.82 mg | 1.1 AU/mg | 2.00 AU |

For the enzyme composition described above in Table 2, collagenase I contributed about 0.7 to about 1.7 Wunsch units of collagenase activity and collagenase II contributed about 23.2 to about 31 Wunsch units of activity. Because thermolysin provided no significant Wunsch activity, the total composition yielded about 24 to about 33 Wunsch units of activity with an average activity of about 30 Wunsch units. The total composition had about 8,500 to about 14,500 FITC casein units of activity with an average activity of about 12,000 FITC casein units. Accordingly, the ratio range of FITC casein units of the composition to Wunsch units of the composition is 8,500/33 to 14,500/24 or about 250:1 to about 600:1 with an average activity ratio of 12,000/30 or about 400:1.

The enzyme composition described above for dissociation of rat liver is expected to perform acceptably for other tissue types as well. As will be apparent to those skilled in the art, some modification may be necessary to optimize the purified enzyme mixture for dissociating specific tissue types, e.g. tissues which contain more collagen may require increased collagenase activity and tissues which contain more non-collagen proteins may require increased protease activity. Similarly, larger or smaller tissue samples might necessitate corresponding adjustments in enzyme activity.

EXAMPLE 3:

DIGESTION OF RAT LIVER FOR THE ISOLATION OF HEPATOCYTES

Purified enzyme composition combinations were tested by their ability to dissociate rat liver into free hepatocytes. Minor modifications of the procedures of Seglen were used for the evaluations (Seglen, Exp. Cell Res. 82, pp.391–398 (1973)). The buffers described below were used in the organ dissociation. All buffers were prepared using high purity water and passed through a 0.2 micron filter to insure sterility.

Perfusion Buffer: 8.3 g sodium chloride, 0.5 g potassium chloride and 2.4 g HEPES were added to 800 ml water. After solution was complete the pH was adjusted to 7.4 and the volume brought to 1,000 ml.

Digestion Buffer: 3.9 g sodium chloride, 0.5 g potassium chloride, 0.7 g calcium chloride dihydrate and 24 g HEPES were added to 800 ml water. After solution was complete the pH was adjusted to 7.6 and the volume brought to 1,000 ml.

Suspension Buffer: 4.0 g sodium chloride, 0.4 g potassium chloride, 7.2 g HEPES, 0.18 g calcium chloride dihydrate, 0.15 g potassium phosphate, 0.1 g sodium sulfate, 0.13 g magnesium chloride hexahydrate, 6.9 g (2- {[tris-(hydroxymethyl) -methyl]-amino}-ethanesulfonic acid) (TES), 6.5 g {N[tris-(hydroxymethyl)-methyl]-glycine} (TRICINE) and 2.1 g sodium hydroxide were added to 800 ml water. After solution was complete the pH was adjusted to 7.6 and the volume brought to 1,000 ml.

Wash Buffer: 8.3 g sodium chloride, 0.5 g potassium chloride, 2.4 g HEPES and 0.18 g calcium chloride dihydrate were added to 800 ml water. After solution was complete the pH was adjusted to 7.4 and the volume brought to 1,000 ml.

Male Wistar rats (150 to 200 g) were anesthetized using I.P. injections of pentabarbitol (10 mg/100 g body weight). The abdominal cavity was opened and the inferior vena cava cannulated between the liver and kidney. The vena cava was ligated above the liver and the portal vein was cut or cannulated to allow for reflux from the liver. The liver was perfused for at least five minutes with perfusion buffer at a flow rate of 30 ml/min. The enzyme composition from example 2 above was dissolved in 300 ml of digestion solution and incubated at 37° C. until warm. The liver was then dissociated by passing the digestion solution through the organ at a flow rate of 30 ml/min until the organ softened. The digestion time was noted.

The softened organ was removed and carefully pulled apart in suspension buffer which was pre-gassed with 95% oxygen and 5% carbon dioxide. Any remaining tissue was cut into small pieces and any blood vessels and membranes were removed. The tissue suspension was brought to a final volume of 150 ml with suspension buffer and incubated with gentle stirring at 37° C. for 25 min to disperse the hepatocytes. After removal of tissue chunks by filtration the hepatocytes were pelleted by centrifugation at 20×G for 5 minutes at 4° C. The non-hepatocyte cells, damaged hepatocytes, and cell debris were located in the supernatant and removed by aspiration and discarded. The hepatocytes were washed and centrifuged at least two additional times with cold wash solution. Final cell count and % viability were determined. Four million hepatocytes were plated on 60 ml diameter collagen coated culture plates and incubated at 37° C. in 95% air and 5% carbon dioxide at 95% relative humidity. Function assays were performed at appropriate time intervals.

EXAMPLE 4:

DIGESTION OF RAT EPIDERMAL FAT FOR THE ISOLATION OF MICROVASCULAR ENDOTHELIAL CELLS

An enzyme composition containing 2.32 mg collagenase II, 3.48 mg collagenase I and 1.82 mg thermolysin was used to dissociate samples of rat fat pad tissue for the purpose of recovering microvascular cells. The procedure used was a minor modification of the procedure of Rodbell (J. Biol. Chem., v. 239, pp. 375 (1964)). The preferred blend composition was reconstituted in 20 ml of physiological phosphate buffered saline (PBS) solution containing 1.0 mg/ml of fatty acid free bovine serum albumin (BSA) and sterilized through a 0.2 micron cellulose acetate filter. Four finely minced epididymal fat pads (fat volume averages 3 to 5 ml) from 8 to 10 week old rats were placed in 10 ml of the enzyme blend solution. Digestion was performed at 37° C. in a shaking water bath for 10 to 15 min. Cells were recovered by centrifugation for four minutes at 700×G. Floating fat and enzyme blend solutions were aspirated and discarded. The endothelial cell pellet was twice suspended in PBS buffer containing 1.0 mg/ml BSA and the cells recovered by centrifugation for four minutes at 700×G with a final centrifugation in plain PBS buffer. The cells were then ready for counting, viability testing, culture or additional fractionation.

What is claimed is:

1. An enzyme composition prepared by combining defined masses of purified proteases comprising collagenase I and collagenase II from *Clostridium histolyticum* and an endoprotease, wherein the ratio of the mass of collagenase II to the mass of collagenase I plus the mass of the collagenase II in the composition is about 0.3 to about 0.6 and wherein the ratio of the total FITC casein activity of the enzyme composition to the total Wunsch units of activity of the masses of collagenase I and collagenase II in the composition is about 130:1 to about 1400:1.

2. The enzyme composition of claim 1 wherein the endoprotease is a neutral protease.

3. The enzyme composition of claim 2 wherein the neutral protease is selected from the group consisting of thermolysin, dispase and *Clostridium histolyticum* neutral protease.

4. The enzyme composition of claim 2 wherein the neutral protease is thermolysin.

5. The enzyme composition of claim 1 wherein the ratio of the mass of collagenase II to the mass of collagenase I plus the mass of the collagenase II in the composition is about 0.35 to about 0.45.

6. The enzyme composition of claim 1 wherein the composition is substantially free of endotoxins.

7. A method of preparing an enzyme composition adapted for isolating living cells from tissue, said method comprising the steps of combining known masses of chromatographically purified collagenase I and collagenase II from *Clostridium histolyticum*, wherein the ratio of the mass of collagenase II to the mass of collagenase I plus the mass of the collagenase II in the composition is about 0.3 to about 0.6, and adding an amount of an endoprotease sufficient to raise the total FITC casein activity of the enzyme composition to a level such that the ratio of the total FITC casein activity of the enzyme composition to the total Wunsch unit activity of the masses of purified collagenase I and collagenase II in the enzyme composition is about 130:1 to about 1,400:1.

8. The method of claim 7, wherein the endoprotease is a neutral protease.

9. The method of claim 8 wherein the neutral protease is selected from the group consisting of thermolysin, dispase, and *Clostridium histolyticum* neutral protease.

10. The method of claim 8 wherein the neutral protease is thermolysin.

11. The method of claim 10 wherein the ratio of the mass of collagenase II to the mass of collagenase I plus the mass of the collagenase II in the composition is about 0.35 to about 0.45.

* * * * *